United States Patent
Ekinci

(10) Patent No.: US 10,352,918 B2
(45) Date of Patent: Jul. 16, 2019

(54) TEST EQUIPMENT DETERMINING CONCRETE COMPRESSIVE STRENGTH CLASS

(71) Applicant: Firat Akademi Yayincilik Egitim Sanayi Ve Ticaret Anonim Sirketi, Elazig (TR)

(72) Inventor: Cevdet Emin Ekinci, Elazig (TR)

(73) Assignee: Firat Akademi Yayincilik Egitim Sanayi Ve Ticaret Anonim Sirketi, Elazig (TR)

( * ) Notice: Subject to any disclaimer, the term of this patent is extended or adjusted under 35 U.S.C. 154(b) by 9 days.

(21) Appl. No.: 15/547,747

(22) PCT Filed: Dec. 24, 2015

(86) PCT No.: PCT/TR2015/050261
§ 371 (c)(1),
(2) Date: Jul. 31, 2017

(87) PCT Pub. No.: WO2016/122425
PCT Pub. Date: Aug. 4, 2016

(65) Prior Publication Data
US 2018/0011077 A1    Jan. 11, 2018

(30) Foreign Application Priority Data
Jan. 29, 2015 (TR) .............. a 2015 00987

(51) Int. Cl.
*G01N 33/38* (2006.01)
*G01N 27/06* (2006.01)
*C04B 40/00* (2006.01)

(52) U.S. Cl.
CPC ........... *G01N 33/383* (2013.01); *G01N 33/38* (2013.01); *C04B 40/0028* (2013.01); *C04B 40/0032* (2013.01); *G01N 27/06* (2013.01)

(58) Field of Classification Search
CPC ........................... G01N 33/383; G01N 33/38
See application file for complete search history.

(56) References Cited

U.S. PATENT DOCUMENTS 3,499,328 A * 3/1970 Kenny et al. ........ G01N 33/383
494/10
2015/0210995 A1 7/2015 Matsui et al.

FOREIGN PATENT DOCUMENTS

| RU | 2013 129956 A | 1/2015 |
| WO | 93/18401 A2 | 9/1993 |
| WO | 2013/175246 A2 | 11/2013 |

OTHER PUBLICATIONS

International Search Report of PCT/TR2015/050261, dated May 9, 2016.

\* cited by examiner

*Primary Examiner* — Herbert K Roberts
(74) *Attorney, Agent, or Firm* — Gokalp Bayramoglu

(57) ABSTRACT

This invention is test equipment for determining a concrete's compressive strength class and characteristic equivalent cube compressive strength value while the concrete is in its fresh concrete period.

Figure 1:
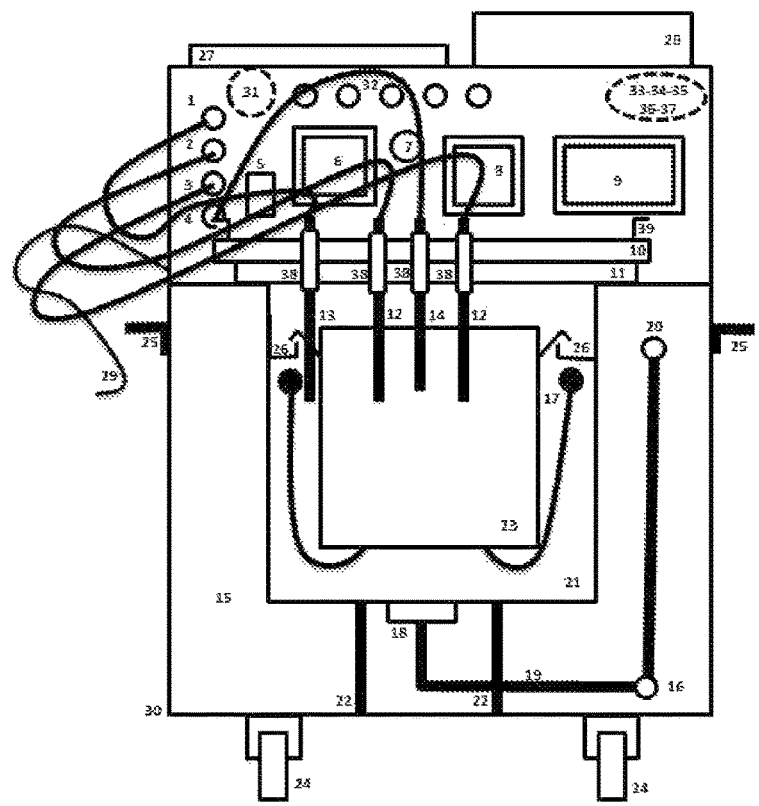

12 Claims, 3 Drawing Sheets

TEST EQUIPMENT DETERMINING CONCRETE COMPRESSIVE STRENGTH CLASS

CROSS REFERENCE TO RELATED APPLICATION

This application is a national application of PCT-application PCT/TR2015/050261 filed on Dec. 24, 2015, which claims priority of Turkish patent application No. 2015/00987 filed on Jan. 29, 2015, both of which disclosures are incorporated herein by reference.

TECHNICAL FIELD

This invention relates to equipment that determines from fresh concrete the concrete's ultimate compressive strength class and characteristic equivalent cube compressive strength value.

PREVIOUS TECHNIC

Numerous national standards relating conventional and ready-mixed concretes' compressive strength classes and characteristic equivalent cube compressive strength values have been prepared. TSEN 206-1, TS500, TS802, TS10465 and TS11222 are examples. In all standards, concrete compressive strength class and characteristic strength values are determined using either cylindrical (15×30 cm) or cube (15×15×15 cm or 10×10×10 cm) samples. Generally, compressive strength values are said to be taken from cube samples.

Concrete, an important and a widespread material in today's construction industry, has entered our lives as a construction material requiring attention and care during every stage of production and practice. Concrete is produced by mixing aggregation (fine and coarse), cement, and water with chemical and mineral additives (homogenously or not, based on production technology) and which has a plastic consistency shortly after having been produced and considerable strength by hardening over time.

High-strength concrete is needed by multi-story buildings because, with a minimum C20/25 compressive strength class, it is used in supporting structural members. Ready-mixed concrete is becoming widespread, and it is highly possible to say that it will in the future replace conventional concrete.

Concrete compressive strength class is found in nine of TS500, sixteen of TSEN206-1, sixteen of TS11222 and nine of TS10465 national standards. Five fundamental steps determine concrete's quality: design, production, transportation, placement, and maintenance and cure. The first three are carried out by the concrete producer and the last two by the consumer.

Concrete additives are introduced during or shortly before the basic materials—cement, aggregation, and water—are mixed. Additives can increase the performance of the concrete, improving properties or economy. Reinforced concrete is the most widely used construction material for transferring vertical and horizontal loads of a framed structure into a floor. Therefore, the concrete used for transferring compression loads into a floor needs to be of a certain concrete class and strength.

Based on TSEN 206-1, concrete's characteristic compressive strength value is "the value where the possibility of being concrete compressive strength less than such value is 5%". On the other hand, concrete's quality is controlled by "Characteristic Strength" (fck).

There are several mix design methods and principals regarding concrete's characteristic strength (fck) and target compression strength (fcm) (design-average strength). ACI211 is an international example. Methods and principals mentioned above present important numerical values and solutions on how much proportion and/or amount of material will be used for a targeted concrete compressive strength class. Concretes produced based on such numerical values do not always give targeted concrete compressive strength class. Thus, it is of vital importance to know concrete's compressive strength class and value at early ages.

Two methods determine concrete's compressive strength. The first method includes taking core samples from hardened concretes, while the second includes taking samples from fresh concrete in the mold stage, and storing samples for 28 days in a cured environment. The first method is not practical. A full-fledged concrete laboratory and technical team are necessary for taking core samples and testing their strength values. Moreover, it is not cost-effective.

The second method also requires a full-fledged concrete laboratory and technical team. Moreover, compressive strength results become available only after 28 days. Thus this method is not practical either due to time management and the curing operation.

In fact, fresh ready-mixed concrete in a plastic consistency stage coming to the construction area is molded and pressed in no more than an hour. Twenty-eight days are necessary to determine molded concrete's compressive strength class and value. At 7 days and 14 days some results about concrete's strength can be obtained by testing it under compression loads, and some predictions about its 28-day-strength value can be made by cycle-conversion factors. Moreover, similar predictions and results also can be obtained by calculations such as maturity in the concrete. But none of these approaches and tests indicates an ultimate result about a concrete's compressive strength class and characteristic equivalent cube strength. All current experimental methods and tests are based on determining concrete's ultimate compressive strength class and value after 28 days. This phenomenon causes serious loss of time. More importantly, if molded concrete is not in the desired compressive strength class, the structure needs to be reinforced or demolished and the mold needs to be prepared and produced again and new concrete needs to be placed into the mold a second time. This phenomenon also causes loss of time and money.

Moreover, support structure elements produced by low-strength concretes do not offer enough strength to additional forces, especially during earthquakes, leading, perhaps, to collapse. Based on these fundamental aspects, and because since 80% of our country lie in Earthquake Zones 1 and 2 and has major earthquake fault lines, it is important to know the ultimate national standards, compressive strength class and value of the concrete in the fresh concrete stage before molding.

As stated above, there are numerous experimental methods and techniques for estimating a concrete's compressive strength values. A majority of these are based on hardened concretes. There has not yet been developed a method for determining concrete's ultimate strength by using its properties as obtained in the fresh concrete stage (plastic consistency). Some predictions about concrete's compressive strength class can be made by taking fresh concretes' physical properties and behaviours into consideration, but these do not give any numerical result.

Concrete's compressive strength class in reinforced-concrete design is an important factor used in reinforced-concrete calculations. Therefore, the term called concrete's characteristic strength (fck), which is defined as the maximum tension load that dimensional samples can carry under unidirectional loads, is used. Target and/or design strength (fcm) is used in cross-section and ultimate bearing capacity calculations. Thus, for the design of reinforced-concrete buildings, the specification and classification of concrete is made based on characteristic strength. While there are other constituents determining concrete class except compressive strength in the table related the standard TS 500 "Requirements for design and construction of reinforced-concrete structures," the aforementioned criteria in the end are related to compressive strength. In other Turkish standards, except the fundamental TS 500, some values asserted about concrete's compressive strength and characteristic values are given in Table 2. In fact, there is no considerable difference among concrete classes defined in Table 2. Differences come more likely from sample dimensions and the availability of different concrete classes.

Some experiments, methods and techniques used for determining concretes' compressive strength are given in Table 1. There are numerous factors affecting concrete's compressive strength:
- Concrete production method
- Water/Cement (Water/Binder) ratio
- Construction chemicals and additives
- Quality of mixing water
- Concrete-batching time and steps
- Rheology and gradation of aggregate
- Grain size and shape of the most coarse aggregate
- Surface texture of aggregate grains
- Harmful substances in the aggregate
- Cement type, amount and age
- Physical and chemical properties of the cement
- Properties and amounts of minerals and chemical additives used in making concrete
- Concrete transportation, placement, and consolidation
- Concrete age
- Temperature and moisture content of the environment where concrete is prepared, poured, and cured Factors mentioned above arise from the materials constituting the concrete and the environment. While constituents of a concrete mix are almost always of the same amount and type, concrete compressive strength results cannot always be obtained during tests. The reasons can be:
- The effect of the length/diameter ratio of cylindrical samples
- The effect of the shape (cube or cylindrical) of the sample
- The effect of dimensions on compressive strength
- The effect of the loading rate on compressive strength
- Properties of construction chemicals and additives
- The effect of the most coarse aggregate's grain size in the mold
- The effect of temperature and moisture within the sample during experiment There are two fundamental methods for determining in-situ concrete's strength, and different techniques are available for both methods. The destructive method includes sampling from hardened concrete, while the non-destructive one involves measuring surface hardness. There are advantages and disadvantages of either method relative to one other. For example, destructive methods can damage the building-structure, are not repeatable, give results alone, are not cost-effective, and have lower standard deviation and error rates. Non-destructive methods however do not damage the structure, are repeatable, do not have meaning alone, and are cost-effective but have higher standard deviation and error rates.

TABLE 1

Experiments, methods and techniques used for determining normal concretes' compressive strength development

| Experiments, Methods and Techniques Used for Determining Hardened Concretes' Compressive Strength | | Factors of Fresh Concretes' Physical Properties Directly |
| --- | --- | --- |
| Non-destructive Experiments, Methods and Techniques | Destructive Experiments, Methods and Techniques | Affecting Compressive Strength Development |
| Compressive Strength Experiment | Mounted Specimen Use Method-Experiment | Segregation |
| Covermeter Test | | Unit Weight |
| Tensile Strength Experiment | Core Sampling Method-Experiment | Resistance-Heat Ratio |
| Flexural Strength Experiment | | Electrical Resistivity |
| Electrical Potential Method | | Expansion |
| Permeability Method | | Air Content |
| Indentation Measurement Experiment | | Machinability |
| Shear Strength Experiment | | Conductivity |
| Magnetic Method | | Consistency |
| Mechanical Sound Wave Velocity (Pulse Echo) Technique | | Porosity |
| Maturity Method | | Initial and Final Setting |
| | | Temperature |
| Penetration (Indentation) Experiment | | Water/Cement Ratio |
| Resonance Frequency Technique | | Water Saturation Degree |
| Ultra Sound Velocity Technique | | Bleeding |
| Surface Hardness Method | | Uniformity |

TABLE 2

Concretes' Compressive Strength Class and Characteristic and Target Strength Values (MPa)

| Concrete Compressive Strength Classes | | | | | | Characteristic Compressive Strength ($f_{ck}$) | | | Target (Design-Average) Compressive Strength ($f_{cm}$) | | Concrete Samples taken in the land ($f_{ck}$) (TS EN 206) | |
|---|---|---|---|---|---|---|---|---|---|---|---|---|
| | | TS | | | | Cylindrical compressive strength | Cube Compressive Strength | Equivalent | If standard | | | |
| TS 500 | TS EN206-1 | 11222 | TS 10465 | TS 802 | Description | (15 × 30 cm) | (15 × 15 cm) | If standard deviation known | deviation not known | | | |
| | | | | | | | | | Cylinder | Cube | Cylinder | Cube |
| | C8/10 | | | | Low- | | | $f_{cm} =$ | | | 8 | 10 |
| | C12/15 | | | | Strength | | | $f_{ck} +$ | | | 12 | 15 |
| | | C14 | BS14 | C14/16 | Concrete | 14 | | 1,48σ | 18 | 20 | | |
| C16 | C16/20 | C16 | BS16 | C16/20 | General- | 16 | 20 | | 20 | 24 | 16 | 20 |
| C18 | | C18 | | C18/22 | Purpose | 18 | 22 | | 22 | 26 | | |
| C20 | C20/25 | C20 | BS20 | C20/25 | Concrete | 20 | 25 | | 26 | 31 | 20 | 25 |
| C25 | C25/30 | C25 | BS25 | C25/30 | | 25 | 30 | | 31 | 36 | 25 | 30 |
| C30 | C30/37 | C30 | BS30 | C30/37 | Normal- | 30 | 37 | | 36 | 43 | 30 | 37 |
| C35 | C35/45 | C35 | BS35 | C35/45 | Strength | 35 | 45 | | 43 | 53 | 35 | 45 |
| C40 | C40/50 | C40 | BS40 | C40/45 | Concrete | 40 | 50 | | 48 | 58 | 40 | 50 |
| C45 | C45/55 | C45 | BS45 | C45/55 | | 45 | 55 | | 53 | 63 | 45 | 55 |
| C50 | C50/60 | C50 | BS50 | C50/60 | | 50 | 60 | | 58 | 68 | 50 | 60 |
| | C55/67 | C55 | | C55/67 | High- | 55 | 67 | | 63 | 75 | 55 | 67 |
| | C60/75 | C60 | | C60/75 | Strength | 60 | 75 | | 68 | 83 | 60 | 75 |
| | C70/85 | C70 | | C70/85 | Concrete | 70 | 85 | | 78 | 93 | 70 | 85 |
| | C80/95 | C80 | | C80/95 | Ultra- | 80 | 95 | | 88 | 103 | 80 | 95 |
| | C95/105 | C90 | | C90/105 | High | 90 | 105 | | 98 | 113 | 90 | 105 |
| | C100/115 | C100 | | C100/115 | Strength Concrete | 100 | 115 | | 108 | 20 | 100 | 115 |
| Note | | | Concrete | | CC | | | | Concrete Class | | | |

BRIEF DESCRIPTION OF THE INVENTION

The invention, which is defined for the standards of the country in which it is to be used, is related to the test equipment whose purpose is to determine concrete compressive strength class and characteristic equivalent cube compressive strength (fck) shown in Table 2 while yet in the fresh concrete stage, i.e. in the first half of the plastic consistency period; the invention improves concrete quality, minimizes the conflicts among parties, and contributes to the quality assurance system in concrete production.

MEANINGS OF THE FIGURES

Figure 2:
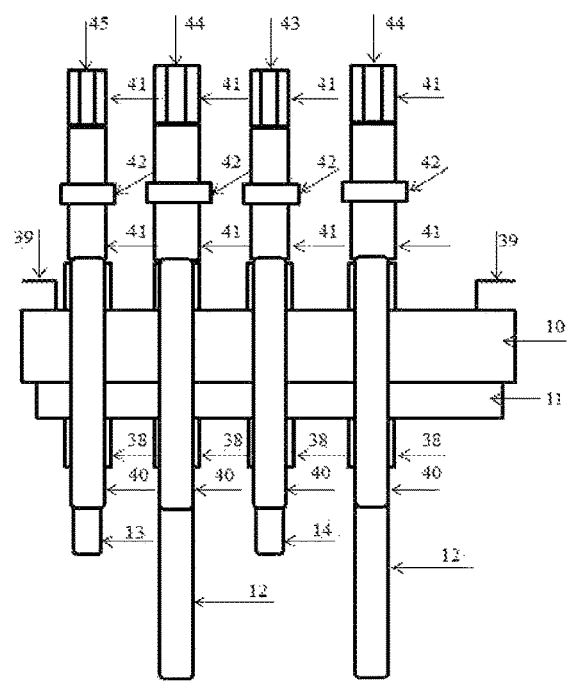
Figure 3:
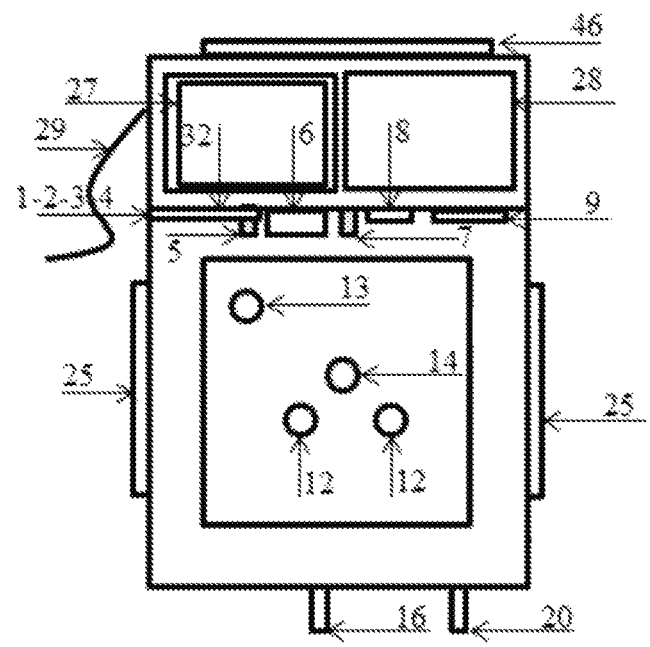
Figure 4:
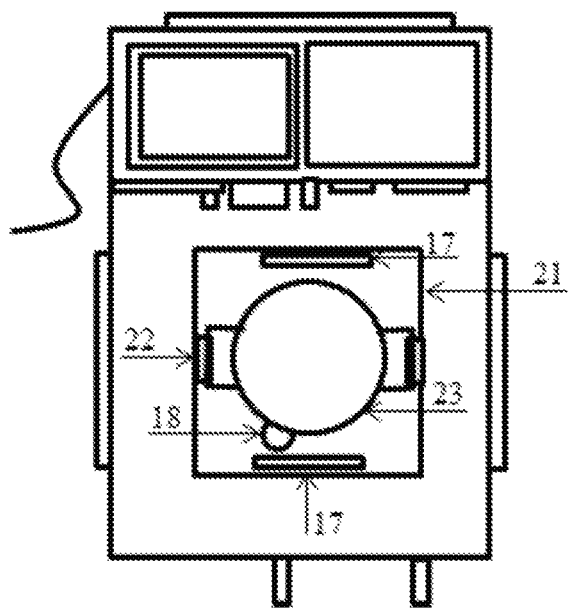
Figure 5:
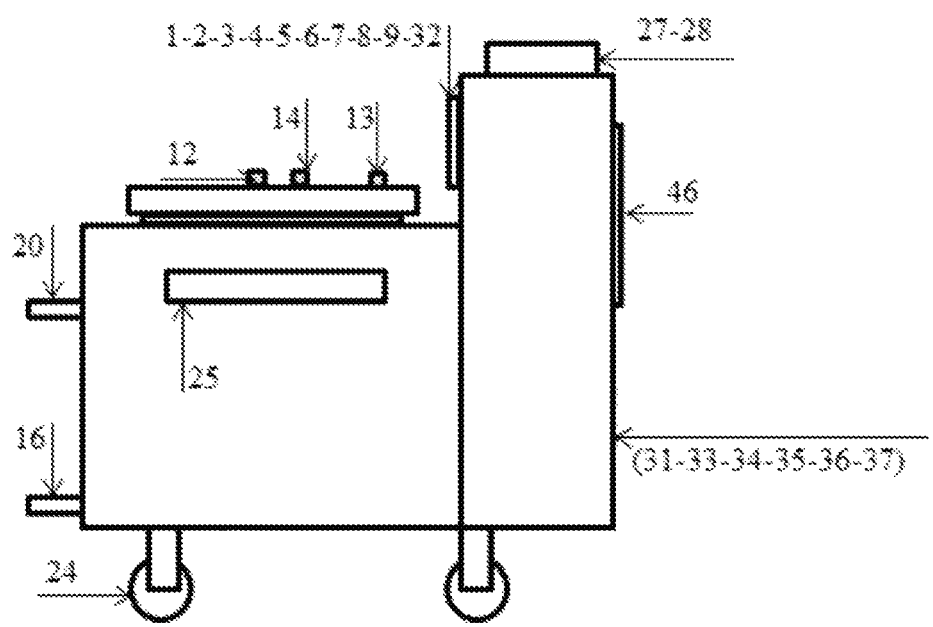

FIG. 1. Frontal View of the Test Equipment
FIG. 2. Cross-section view of the concrete cabin cover
FIG. 3. Top view of the test equipment (cover closed)
FIG. 4. Top view of the test equipment (cover open)
FIG. 5. Side view of the test equipment The equivalents of the part numbers stated on the figures are given below 1. Fresh Concrete Thermometer Entry/Exit Point
2. Electrical Resistivity Meter (+) Entry/Exit Point
3. Electrical Resistivity Meter (−) Entry/Exit Point
4. Heat Treatment J-Type Thermocouple Entry/Exit Point
5. Energy Power Button
6. Digital Heat Control Equipment
7. PLC Controller Power Button
8. Data Entry Control Keyboard
9. LCD Result Screen
10. Chrome Cover
11. Silicon-based Tubular Joint Ring
12. Electrical Resistivity Chrome Measure Probes and Hoses
13. J-Type Thermocouple Probe and Hose
14. Fresh Concrete Thermometer Probe and Hose
15. Heat Insulation
16. Water Disposal System
17. Water Heater Resistance
18. Water Precipitation Point/Fixture
19. Steel Spiral Hose
20. Water Balance and Disposal System
21. Water Tank
22. Water Tank Transporter Cantilevers
23. Fresh Concrete Bucket
24. Rubber Wheels
25. Testing Set Transporter and Routing Levers
26. Fresh Concrete Bucket Transporter and Holding Shanks
27. Chrome Bath
28. Balance
29. Electrical Energy-Power Pack
30. System Storage-Maintain Case
31. Contactor
32. System Operational Lighting
33. Microprocessor Card-PLC
34. Empirical Equation
35. Power Pack Transducer
36. Temperature Sensor
37. Electrical Resistivity Sensor
38. Anchored Chrome Pipes for protecting Probe-Measure Members
39. Cover Opening/Closing Chrome Handle
40. Plastic Insulation Sheath and Hose
41. Rubber Joint Ring 42. Measure Cable Threaded Joint Apparatus
43. Concrete Thermometer Cable
44. Electrical Resistivity Meter Cable
45. Heat Treatment Thermometer Cable
46. Operating System Cabin Cap

DETAILED DESCRIPTION OF THE INVENTION

The invention includes a fresh concrete thermometer entry/exit point (1), electrical resistivity meter (+) entry/exit point (2), electrical resistivity meter (−) entry/exit point (3), heat treatment J-type thermocouple entry/exit point (4), energy power button (5), digital heat control equipment (6), PLC controller power button (7), data entry control keyboard (8), LCD result screen (9), chrome cover (10), silicon-based tubular joint ring (11), electrical resistivity chrome measure probes and hoses (12), J-type thermocouple probe and hose (13), fresh concrete thermometer probe and hose (14), heat insulation (15), water disposal system (16), water heater resistance (17), water precipitation point/fixture (18), steel spiral hose (19), water balance and disposal system (20), water tank (21), water tank transporter cantilevers (22), fresh concrete bucket (23), rubber wheels (24), testing set transporter and routing levers (25), fresh concrete bucket transporter and holding shanks (26), chrome bath (27), balance (28), electrical energy-power pack (29), system storage-maintain case (30), contactor (31), system operational lighting (32), microprocessor card-PLC (33), empirical equation (34), power pack transducer (35), temperature sensor (36), electrical resistivity sensor (37), anchored chrome pipes for protecting probe-measure members (38), cover opening/closing chrome handle (39), plastic insulation sheath and hose (40), rubber joint ring (41), measure cable threaded joint apparatus (42), concrete thermometer cable (43), electrical resistivity meter cable (44), heat treatment thermometer cable (45), and operating system cabin cap (46) parts.

Determination of concrete's compressive strength and class by current systems and approaches is very long process taking 28 days. Moreover it causes sophisticated and serious problems. Determining with high accuracy of fresh concrete's compressive strength and class in 30 minutes before molding via the test equipment of our invention will make major contributions to control and inspection and be helpful to related parties. Buildings will be made earthquake-resistant and livable by preventing the use of low-strength concretes.

This invention includes the test equipment for determining within the first 30 minutes of the plastic consistency stage the concrete's compressive strength class and characteristic equivalent cube compressive strength value otherwise obtained after 28 days.

Determination of concretes' compressive strength and class in the fresh concrete stage will contribute to local governments actively participating in the construction sector as well as to building audit companies. One of the most significant subjects that people working in the control aspect of the construction sector commonly encounter is the concern whether the concrete will achieve desired compressive strength and class (project aim). This concern, mostly occurring between control members and producing companies, will be completely relieved. Moreover, the equipment use will form a basis for achieving ready-mixed concretes' compressive strength as specified in the project aim. Consequently, buildings should be strengthened. Moreover, it is hoped that questions of law occurring during the use of concretes not satisfying desired strength will be eliminated. Not only will waiting time be reduced from a month to 30 minutes, but also the use of low-strength concretes will be prevented.

Producing the concrete used in reinforced-concrete applications, which is the constituent of many buildings' undercarriage, in accordance with high quality and compressive strength class is of vital importance to our country, the majority of which is in the seismic belt. Accordingly, information about concrete materials has been increasing; as a result, aggregates, anchors, additives, and concrete construction, casting, and protection requirements have to satisfy minimum standards.

The invention's test equipment is created by two main parts: the "Concrete cabin" and the "Operating system cabin." The concrete cabin has a chrome mobile cover (10) with a minimum 2-mm internal wall and a silicon-based tubular joint ring (11). The operating system, on the other hand, has a cap screwed from the back (46).

There are also an LCD result screen (9), data entry control keyboard (8), digital heat control equipment (6), PLC controller power button (7), energy power button (5), fresh concrete thermometer entry/exit point (1), electrical resistivity meter entry/exit point (2), heat treatment J-type thermocouple entry/exit point (4), system operational lighting (32) and contactor control key (31) on the front of the operating system.

There are a trowel, rodding apparatus, grading apparatus, molding and cleaning members to be used during the experiment, chrome bath (27) for protection, and weighing machine (28) on the top of the operating system.

There are a microprocessor card-PLC (33), empirical equation (34), power pack transducer (35), temperature sensor (36), electrical resistivity sensor (37), and power pack contactor (31) inside the operating system cabin.

There are water-tight chrome tank, two vertical opposing water heater resistances, heat-insulated water tank, water precipitation and disposal part under the floor of the water tank's inner surface, fresh concrete steel bucket and chrome hangings mechanics inside the concrete cabin.

There are a water disposal-relief valve connected with the water tank and water balance and disposal system in the same horizontal level with the concrete bucket on the front and lower part of the concrete cabin.

There are transporter and routing levers and apparatus on the left and right side of the concrete cabin.

There is an air-sealed and 5-cm-thick cover made up of chrome on the upper portion of the concrete cabin. There are four measurement points and two opening/closing handles on the cover. All measurement points were made up of chrome pipe. Measurement points in a triangle shape are positioned at a 5-cm distance in the middle of the cover. Another measurement point at the back of the cover is for a heat treatment temperature probe while measurement points in the middle are for fresh concrete temperature and electrical resistivity probes. Length of measurement probe cable is between 50 and 70 cm and cables are passed through protection-cover hoses. Cables are set into particular insulated-hoses and there are particular insulation joint rings on the probe's ends. The electrical energy power pack port is a grounding system and on the right-hand side.

The working principle of our test equipment can be explained as follows: At least 10 dm3 volume of fresh concrete is necessary for evaluating the concrete's compressive strength class. The test equipment with its testing set transporter and routing levers (25) rides on rubber wheels (24), and is meant to be on a smooth surface and should be immobilized by locking its wheel stoppers. There is heat insulation of no less than 10-mm thickness between the water tank (21) and system storage-maintain case (30). The water tank is an internal disposal water precipitation (18) system. The water precipitation system is connected to the water disposal system (16) and water balance and disposal system (20) through a steel spiral hose (19). There is a chrome bath (27) embedded on the operating system. Electrical energy is supplied by a power pack entry (29) to operate the equipment. The power pack is connected with contactor (31) and power pack transducer (35) inside the operating system cabin (29). There are a contactor (31), microprocessor card-PLC (33), empirical equation (34), power pack transducer (35), temperature sensor (36) and electrical resistivity sensor (37) intercorrelated with other inside the operating system cabin. The water tank (21) is connected to the system maintain case through the water tank transporter cantilevers (22).

The concrete, whose compressive strength class will be determined by the test equipment, is first poured into the fresh concrete bucket (23) in three equal stages. It is provided that every stage will be fogged at least 25 times. Excess concrete on the fresh concrete bucket is stripped, weighed on a balance (28) and its unit weight (density) is calculated based on the laws and regulations of the region in which the concrete will be used. The calculated unit weight is processed into an empirical equation (34) in the microprocessor card (33) inside the operating system cabin by the data entry control keyboard (8). After the water disposal system (16) is closed, 25 liters of drinkable water is poured into the fresh concrete bucket (23). When the concrete cabin (21) is full of water, the concrete bucket (23) filled with fresh concrete is properly placed by concrete bucket transporter and holding shanks (26). The excess water above 25 liters inside the concrete cabin (21) is removed by the water balance and disposal system (20). Additional water is added into the concrete cabin taking care to total 25 liters in the case of deficient water. The concrete cabin cover (10, 11) is closed by the cover-closing chrome handle (39).

The electrical resistivity chrome measurement probes (2, 3, 12, 40, 41, 42, 44) are embedded into the fresh concrete through measurement holes (38) in the chrome cover (having a minimum 2-mm internal wall (10)) by twisting widely and slowly. Later, this same operation is repeated for the fresh concrete thermometer probes (1, 14, 40, 41, 42, 43, 44). To control and monitor the temperature change inside the concrete cabin, J-type thermocouple probes (4, 13, 40, 41, 42, 45) are pushed down inside the water tank (21) through measurement holes (38) on the chrome cover, which as a minimum 2-mm internal wall (10).

The first energy power circuit (5) and then the PLC controller power buttons (7) are opened. The system operational-process lighting (32) is automatically included in the circuit. The temperature of the water inside the water tank (21) is meant to reach 40±2° C. in 10 minutes in a controlled manner through digital heat control equipment (6) by heating two vertical opposing water heater resistances (17) placed into the energy power circuit (5) and water tank (21). Temperature and electrical resistivity values at 15, 20 and 25 minutes are sent to the LCD result screen (9) through probes inside the fresh concrete (12, 14) by operating the system synchronously via the data entry control keyboard (8). These results are processed into the empirical equation (34) in the microprocessor card (33) and then the hardened condition possible compressive strength class that the fresh concrete can have is shown on the LCD result screen (9). The operation is ended.

What is claimed is:

1. An apparatus for testing concrete comprising:
a main housing comprising an opening;
a plurality of rubber wheels coupled to a bottom surface of the main housing;
a mobile cover coupled to the main housing and covering the opening of the main housing, wherein the mobile cover is made of chrome and has a width of at least 2 mm;
a silicon-based tubular joint ring disposed between the mobile cover and the main housing;
a plurality of apertures configured to support a plurality of probes, wherein each one of the plurality of apertures extends through the mobile cover and the joint ring;
a water tank having a bottom opening and disposed inside the main housing;
at least one water heater disposed inside the water tank;
a fresh concrete bucket disposed inside the water tank;
a plurality of holding shanks coupled to the fresh concrete bucket, wherein the holding shanks couple the fresh concrete bucket to the water tank and support the fresh concrete bucket within the water tank;
a thermally insulating material disposed between the water tank and the main housing;
a water removal system coupled to the bottom opening of the water tank and configured to remove water from the water tank, wherein the water removal system comprises a steel spiral hose; and
a weighing scale disposed on a top of the main housing.

2. The apparatus of claim 1, further comprising a plurality of transporting levers coupled to an exterior surface of the main housing.

3. The apparatus of claim 1, wherein the plurality of probes comprises at least one electrical resistivity probe.

4. The apparatus of claim 1, wherein the plurality of probes comprises at least one J-type thermocouple probe.

5. The apparatus of claim 1, wherein the plurality of probes comprises a fresh concrete thermometer probe.

6. The apparatus of claim 1, further comprising at least one handle coupled to the mobile cover.

7. The apparatus of claim 1, further comprising a plurality of plastic sheaths, each one of the plurality of plastic sheaths being disposed between a corresponding one of the plurality of apertures and a corresponding one of the plurality of probes.

8. The apparatus of claim 1, further comprising a power pack configured to supply electrical energy to the plurality of probes.

9. The apparatus of claim 1, further comprising a LCD screen and a data entry keyboard coupled to the main housing.

10. The apparatus of claim 9, wherein the LCD screen is configured to display data received from the plurality of probes.

11. The apparatus of claim 9, further comprising a power pack configured to supply electrical energy to the plurality of probes and the LCD screen.

12. The apparatus of claim 1, wherein the at least one water heater disposed inside the water tank comprises a first water heater disposed on a first inner wall of the water tank and a second water heater disposed on a second inner wall of the water tank, the first inner wall being opposite the second inner wall.

* * * * *